United States Patent [19]
Mellbin et al.

[11] Patent Number: 6,029,421
[45] Date of Patent: Feb. 29, 2000

[54] METHOD OF QUALITY CONTROL AND APPROPRIATELY PREPARED PACKAGING CONTAINER AND BLANK

[75] Inventors: Paul Mellbin, Malmö, Sweden; Paolo Benedetti, Modena, Italy

[73] Assignee: Tetra Laval Holdings & Finance S. A., Pully, Switzerland

[21] Appl. No.: 08/973,585

[22] PCT Filed: Jul. 19, 1996

[86] PCT No.: PCT/SE96/00964

§ 371 Date: Dec. 5, 1997

§ 102(e) Date: Dec. 5, 1997

[87] PCT Pub. No.: WO97/07025

PCT Pub. Date: Feb. 27, 1997

[30] Foreign Application Priority Data

Aug. 18, 1995 [SE] Sweden ................................ 9502880

[51] Int. Cl.[7] .................................................. B65B 57/00
[52] U.S. Cl. ................................ 53/410; 53/53; 73/52
[58] Field of Search ................... 53/53, 410; 73/52, 73/74; 324/557

[56] References Cited

U.S. PATENT DOCUMENTS

| | | | |
|---|---|---|---|
| 3,855,531 | 12/1974 | Fielibert et al. | 73/52 |
| 4,243,932 | 1/1981 | Kakumoto et al. | 73/52 |
| 4,657,175 | 4/1987 | Mårtensson . | |
| 4,711,368 | 12/1987 | Simons | 324/557 |
| 4,803,868 | 2/1989 | Vinton et al. | 73/52 |
| 4,914,395 | 4/1990 | Hamada | 324/557 |
| 5,378,991 | 1/1995 | Anderson et al. . | |

FOREIGN PATENT DOCUMENTS 2323639  1/1975  Germany ................................ 53/53

*Primary Examiner*—Linda Johnson
*Attorney, Agent, or Firm*—Burns, Doane, Swecker & Mathis, L.L.P.

[57] ABSTRACT

A method of carrying out quality control of a packaging container or packaging container blank comprises providing a package or blank having one or more poles (12) for interconnection with electric quality control equipment (24). The packaged product (20) will be directly or indirectly electrically accessible, whereby both the quality of the packed product and the tightness of the surrounding packaging container (1) may be determined in a rational and partly automated manner. This is of particular importance in the production of aseptic packaging containers for, for instance, ready-made, heat-treated soups or similar foods.

10 Claims, 2 Drawing Sheets

METHOD OF QUALITY CONTROL AND APPROPRIATELY PREPARED PACKAGING CONTAINER AND BLANK

TECHNICAL FIELD

The present invention relates to a method of quality control of contents or packaging containers after filling and sealing of a packaging container of the type that is produced by forming of a flexible packaging material. The present invention also relates to the non-destructive quality control of contents or prepared packaging containers, as well as a blank for the packaging container.

BACKGROUND ART

Commercially sterile-treated food products, for example milk products or juice, are nowadays often packed in consumer packages which are manufactured from previously sterilized or sterile-treated packaging material. One typical such package is the parallelepipedic packaging container principally for liquid contents which is known under the name Tetra Brik Aseptic® which is manufactured by folding and heat sealing of web-shaped packaging laminate. The packaging laminate comprises layers of fibre material, for example paper, which are coated on either side with thermoplastic material, normally polyethylene. On that side of the packaging laminate which is to be turned to face towards the contents of the container, there is also a layer of a suitable barrier material, normally aluminium foil, which in turn is coated with a thermoplastic layer.

In the manufacture of parallelepipedic packaging containers of the above-mentioned type, use is made of packaging or filling machines which are fed with the packaging material in web form. The packaging material web is sterilized on its passage through the packaging machine in that its surface is coated with a chemical sterilization agent, e.g. hydrogen peroxide, which is subsequently once again removed mechanically from the surface or is vaporised by heat. Hereafter, the packaging material web is reformed while being located in a closed, sterile space, into tube form whereafter the tube is filled with previously sterilized contents and is transversely sealed and severed into cushion-shaped, filled and sealed packaging containers. These are then reformed by mechanical processing into substantially parallelepipedic form. The contents have normally been sterilized beforehand by heat treatment, so-called UHT treatment (ultra high temperature). Because of the relative absence of bacteria, packaging containers produced by such means enjoy an extremely long shelf life even when stored at room temperature. Although the manufacturing method is extremely well-tested and reliable, it cannot, of course, be guaranteed with absolute certainty that all the packages in any batch of any size be sterile. It is therefore normal to undertake, during production, certain controls with a view to establishing the quality of the packed product from the aseptic point of view. Normally, this known control is effected in that a number of newly produced packaging containers are stored for a predetermined time at suitable temperature (e.g. 7 days, 30° C.). After the predetermined storage time, the packaging containers are opened and inspection is carried out of the contents of the package by measuring the pH, by plating on culture medium or by other suitable method for detecting the micro biological growth in the product. Since micro biological growth changes the electrical properties of the substrate, this test can also be put into effect in practice in that, after the packaging containers have been stored at a suitable temperature for a predetermined amount of time (e.g. 2 days, 30° C.), a certain quantity of product from each opened packaging container is poured into a special measurement cell, either containing culture medium or not, where micro biological growth can be detected from the change in electrical properties (conductance and/or capacitance and/or impedance).

In connection with the above-mentioned inspection and control of the quality of the contents (or separately), inspection and control are often carried out of the tightness of the packaging container wall or the material. In order, as far as is possible, also to cover damage which may have occurred during the forming processing work, such inspection and control are normally carried out in the form of a destructive control in connection with the above-mentioned control of the quality of the contents. This control principally focuses on the inner thermoplastic layer of the packaging laminate, since any possible leakage in this layer may entail that the contents reach the barrier layer (the aluminium foil) or the fibre layer, in which event the other barrier properties of the laminate are lost, even if no actual liquid leakage occurs through the laminate. This type of liquid tightness control has hitherto been difficult and time-consuming to carry out with reasonable demands on reliability and costs.

As will have been apparent from the foregoing discussion, the known testing and control method principally suffers from the drawback that all tested packaging containers must be opened and so destroyed. Thus, previously incubated packaging containers which do not display any unacceptable micro biological growth (or leakage) are also lost, which naturally occasions unnecessary costs and work. Hence, it is desirable in the Art to be able to provide a method for quality control of contents or packaging containers of the above-outlined type which considerably reduces loss and costs in connection with quality control of produced packaging containers.

SUMMARY OF THE INVENTION—OBJECTS AND SOLUTIONS

One object of the present invention is, therefore, to realise a method of quality control of contents or packaging containers which does not suffer from the above-considered drawbacks but instead makes it possible in a simple, rational and non-destructive way, to control a selection of packaging containers after filling and sealing without all of the controlled packaging containers and their contents being lost or negatively affected in respect of tightness, sterile properties or commercial value.

A further object of the present invention is to realise a method of quality control which is simple and rational and which may be carried into effect at relatively low cost.

Still a further object of the present invention is to realise a control method which is suited for automatic quality control of produced packaging containers.

These and other objects have been attained according to the present invention in that a method of the type disclosed by way of introduction has been given the characterizing feature that the inside of the packaging container is made electrically accessible by means of a conductive bridge which serves as a pole and, together with a second pole placed at another part of the packaging container, is utilized for measuring the electrical properties through the product or the packaging material wall.

Yet a further object of the present invention is to realise a packaging container which is prepared for non-destructive quality control of contents or container.

Thus, it is a further object of the present invention to realise a packaging container which displays means for allowing connection to external quality control equipment without the packaging container being destroyed or otherwise rendered in such condition that cannot be further employed but loses its commercial value.

Still a further object of the present invention is to realise a packaging container which makes for quality control by electrical means of the contents of the packaging container or of the packaging container proper.

Yet a further object of the present invention is to realise a packaging container which is prepared for quality control in accordance with the method of the present invention, but which nevertheless only insignificantly deviates from a conventional packaging container which is not equipped for quality control.

The above and other objects have been attained according to the present invention in that a packaging container of the type disclosed by way of introduction has been given the characterizing feature that it includes at least one pole for connection to electric measurement equipment, the pole comprising an electric bridge connecting the interior of the packaging container with its ambient surroundings.

Still a further object of the present invention is to realise a blank for manufacture of the above-disclosed packaging container. According to the present invention, this has been achieved in that a blank for producing packaging containers of the above-disclosed type has been given the characterizing feature that it includes a web- or sheet-shaped packaging material which displays an electrically conductive bridge which is connected to at least one side of the material.

ADVANTAGES

Both the method and the packaging container (in finished package or blank form) according to the present invention make for the non-destructive quality control of the contents of the finished packaging container and/or the integrity of the finished packaging container proper. In the first-mentioned case, the micro biological quality of the packed product can be controlled and verified by electric measurement using per se known measurement equipment via the poles or bridges provided according to the present invention, and in the second case, the liquid- or bacteria-tightness of the packaging material can be controlled and verified in that the above-mentioned electric measurement equipment is connected on the one hand to a pole or bridge and, on the other hand, to an electrically conductive layer included in the packaging lamninate. In both cases, the measurement may be carried out simply and efficiently without any damage—either to the packaging container or its contents—and the method is therefore also eminently suitable for semi- or fully-automatic control of a selection of packaging containers produced in a conventional manner.

BRIEF DESCRIPTION OF THE ACCOMPANYING DRAWINGS

Preferred embodiments of both the method and the apparatus according to the invention (i.e. the control method and the packaging container, or alternatively the packaging container blank) will now be described in greater detail hereinbelow, with particular reference to the accompanying, schematic Drawings which illustrate only those parts and details essential to an understanding of the invention. In the accompanying Drawings.

DESCRIPTION OF PREFERRED EMBODIMENTS

The present invention will now be described in a form adapted for employment in a per se known packaging container of parallelepipedic type (Tetra Brik Aseptic®). This package type is well-known and is manufactured by folding and sealing of a web-shaped packaging laminate. Both the packaging container and its manner of manufacture are described in greater detail in, for example, European Patent EP 91712, to which reference is now made. Since the packaging container in itself is not a germane part of the present invention, its construction and design will be considered only in part below. Naturally, the present invention may also be employed in other types of packaging containers, in particular all such containers as are formed by folding and sealing of the packaging laminate.

Figure 1:
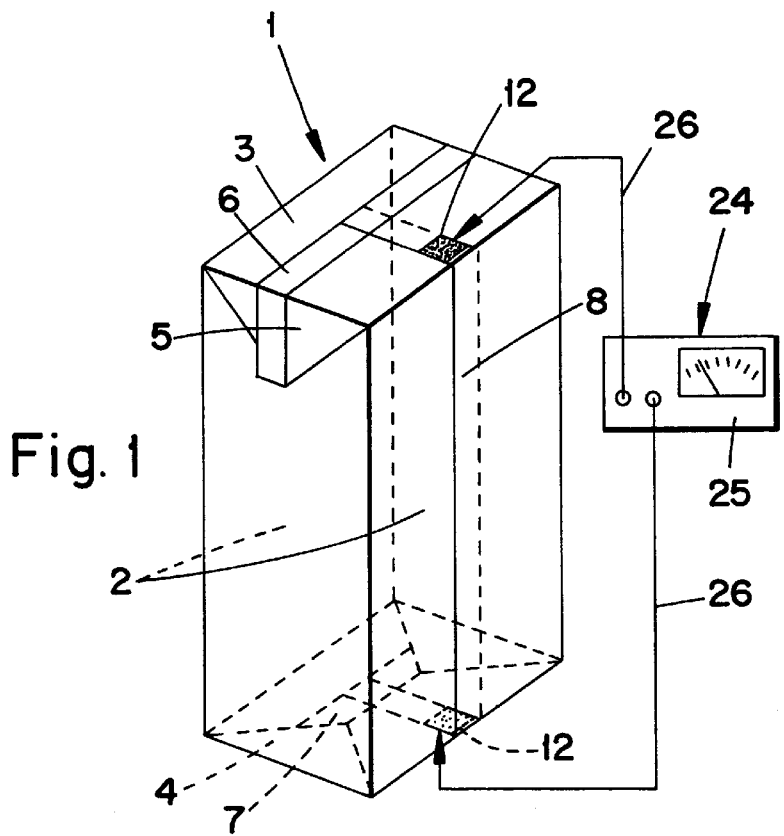
FIG. 1 shows, in perspective and partly in section, a per se known parallelepipedic packaging container which has been equipped and arranged for conducting a quality control according to a first embodiment of the present invention.
Figure 2:
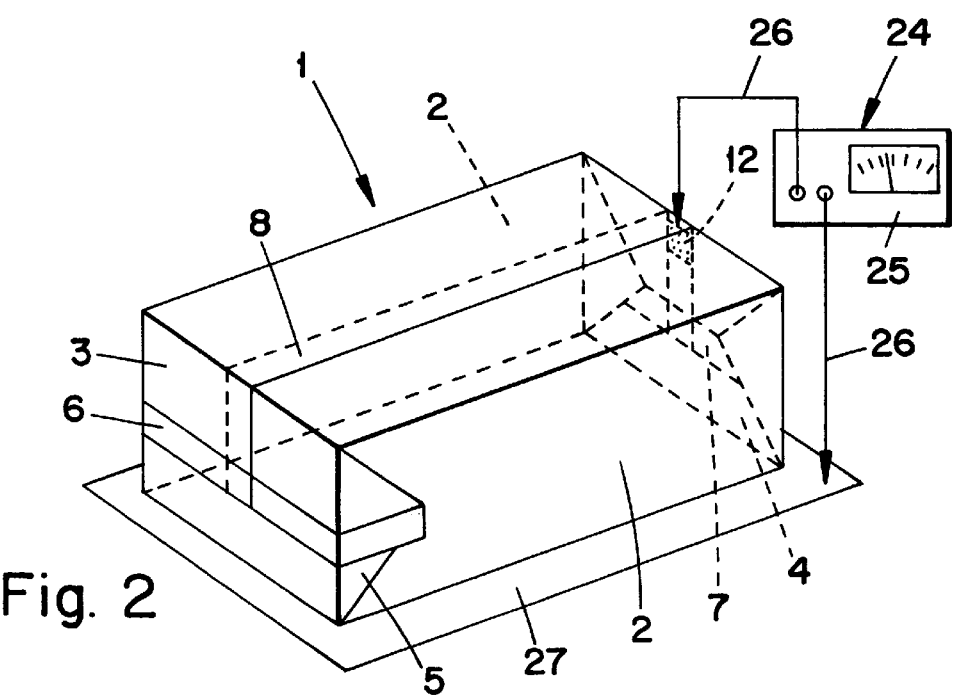
FIG. 2 shows, in perspective and partly in section, a per se known parallelepipedic packaging container which has been equipped and arranged for conducting a quality control according to a second embodiment of the present invention.

FIGS. 1 and 2 show schematically and partly in section how a packaging container of the above-disclosed type is arranged when the method according to the present invention is reduced into practice. The parallelepipedic packaging container 1 comprises a number of side walls 2 and a top surface 3 and bottom surface 4. In the transition between the top and bottom surfaces 3, 4, respectively and the side walls 2, there are four triangular corner flaps 5 which have been pressed flat and connected to the outside of the packaging container 1, for which reason the packaging container is of substantially parallelepipedic configuration. Transverse sealing joints or seams 6 and 7 extend over the top and bottom surfaces 3 and 4 of the packaging container, and a vertical, longitudinal sealing joint 8 extends between these transverse joints along the one side wall 2 of the packaging container.

Figure 5:
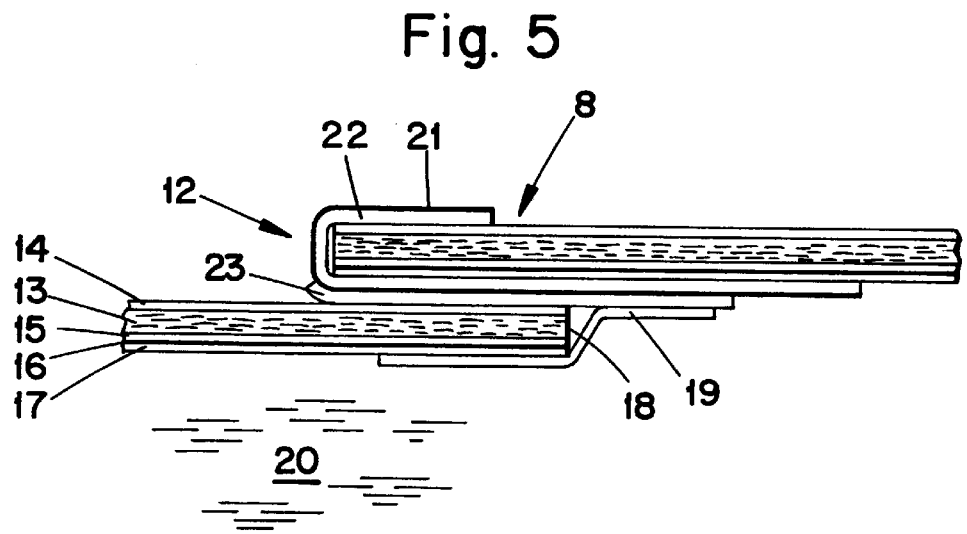
FIG. 5 shows, on a larger scale, a section through the electrically conductive bridge of FIG. 4 placed in a sealing seam or joint in a packaging container according to FIG. 1 or 2.

The per se known packaging containers shown in FIGS. 1 and 2 are both manufactured from a web-shaped packaging material or laminate 9 (FIG. 3) which includes a number of crease lines 10 so as to facilitate reforming to the desired packaging container form. Each individual packaging container utilizes a section of the web which is defined by two indicated incision or section lines 11. A number of transversely extending bridges 12 are applied along the one longitudinal edge of the packaging lamninate web 9, these bridges preferably being folded around the above-disclosed longitudinal web edge and also connected to the opposite surface of the packaging laminate 9, as will be described in greater detail below. A part of the packaging laminate 9 is shown in section in FIG. 5 which is a section through that portion of the packaging laminate which, after reforming into individual packaging containers, includes the sealing joint 8. It will be apparent from the Figure that the packaging laminate includes a relatively thick, inner layer 13 of fibre material, for example paper, which is coated on either side with layers 14, 15 of thermoplastic material, for example polyethylene. On that side of the packaging laminate which is turned to face towards the interior of the packaging container, there is disposed a further layer 16 of suitable barrier material, for example aluminium foil, which, in order to prevent contact with the contents of the packaging container, is coated with an additional layer 17 of thermoplastic material, for example polyethylene. This thermoplastic layer 17 ensures that the material is liquid- and bacteria-tight, but also serves (together with the external thermoplastic layer 14) as sealing material which makes possible heat sealing of the packaging laminate, int. al. to itself, as is the case in the longitudinal and transverse sealing seams or joints 8, 6, 7 of the packaging container. It will also be apparent from FIG. 5 how the incision edge 18 of the packaging laminate facing towards the contents of the packaging container is, for purposes of preventing the absorption of contents into the fibre layer, covered with a covering strip 19 which extends throughout the entire length of the longitudinal sealing joint 8 and which is manufactured from a liquid-tight material which is sealable against the inner thermoplastic layer 17 of the packaging laminate, for example polyethylene. Together with the interior thermoplastic layer 17, the covering strip 19 forms a closed, liquid-tight packaging container space for the contents 20 which may, for instance, consist of milk or juice. Since the packaging laminate 9 has, in connection with the reforming into individual packaging containers filled with contents, also undergone sterilization treatment, the interior of the packaging container is in practice a sterile space which, if it is filled with likewise sterile-treated contents, prevents micro biological growth in an efficient manner and makes possible storage of the packed contents at room temperature for a protracted period of time without any deterioration in the quality of the contents.

In order to control and verify the quality of the packed product, as well as the tightness of the packaging material, use has hitherto been made of so-called destructive testing, in which a number of sample test packaging containers are opened after a certain incubation time, and the quality of their contents (possibly previously incubated) is controlled manually. Similarly, control and verification of the tightness of the packaging laminate and, in particular the internal thermoplastic layer 17 is effected manually, either after rupturing the produced packaging container or breaking the material web immediately before the packaging containers are produced. In both cases, an uncertainty factor is introduced, since, on rupture or reforming into packaging containers, respectively, damage which has been caused or is concealed cannot be discovered.

A technique of electrically controlling and verifying the quality of the product is previously known in the art and is based on the fact that micro biological growth changes the electrical properties of the product, normally in that micro biological growth increases the conductance or capacitance of the contents and entails a total reduction of impedance. This is because of the chemical changes which are caused by the micro-organisms and entails an increased concentration of charge-carrying molecules and/or mobile charge carriers. This technique is described in detail in the literature in the art, for example Firstenberg-Eden; R, and Eden, G: Impedance Microbiology, John Wiley & Sons Inc., 1984. However, employment of this technique necessitates the removal of the contents and their placing in a measurement vessel. The present invention obviates this need and makes possible direct electrical product quality control in unopened packaging containers. In a modified embodiment, control is also made possible of the integrity of the packaging container, i.e. the tightness of the packaging laminate, in a non-destructive manner in an unopened packaging container.

Figure 4:
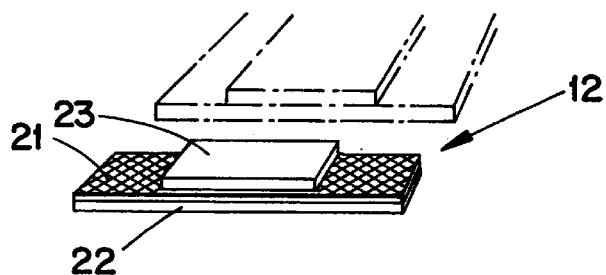
FIG. 4 shows, in perspective and on a larger scale, an electrically conductive bridge of the type which is employed in carrying out the method according to the invention.

In order to carry out the method according to the present invention in a parallelepipedic packaging container of previously known type, the prior art packaging container according to the invention is equipped with the bridges 12. Each bridge 12 includes an electric conductor 21 (FIG. 4) of a conductive material which is inert in relation to the contents of the packaging container e.g. nickel. Throughout all of its one side, the conductor is coated with an insulating layer 22 which, for example, may be polyethylene. On the opposing side, there is a similar insulating layer 23 which, however, is shorter than the conductor 21 and thus leaves this uninsulated at both ends of the bridge 12. If necessary, an adhesive or binder of suitable type may be employed between the two insulating layers 22, 23 and the conductor 21.

Figure 3:
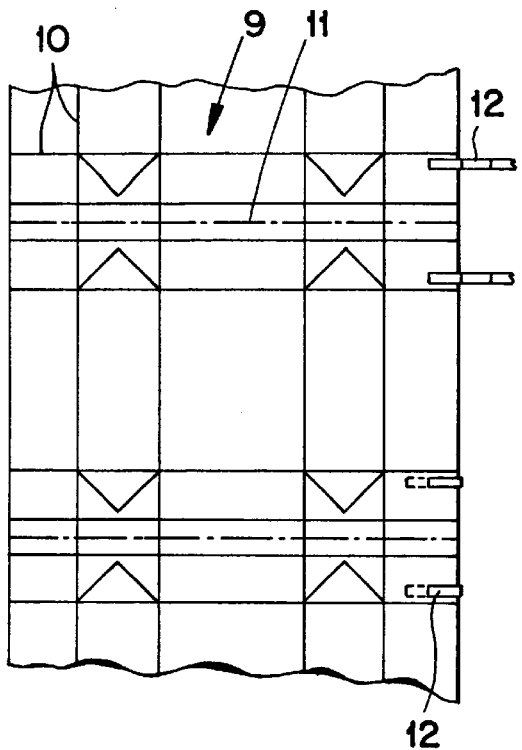
FIG. 3 shows a part of a packaging material web with blanks which have been provided with poles in accordance with the present invention.

While the packaging laminate is still in web form, the bridges 12 are placed with uniform spacing along the packaging material web and are sealed to its one, longitudinal edge. In such instance, the bridges 12 are placed with the insulating layer 22 against the outside of the packaging laminate web 9 and are then folded (as shown in FIG. 3) around the longitudinal edge and sealed by heating and compression also against the opposing side of the packaging laminate which will subsequently face towards the contents of the package. Since both the insulating layer 22 of the bridge 12 and the external layer of the packaging laminate consist of thermoplastic, preferably polyethylene, this application can be put into effect by a simple, per se known heat sealing operation. This technique is also previously known and is not likely to need any detailed description in this context.

When the packaging laminate web 9 provided with bridges 12 is converted in a per se known manner into filled, parallelepipedic packaging containers of the type illustrated in FIGS. 1 and 2, the longitudinal edge provided with the bridges 12 has, by means of an overlap seal, been united in liquid-tight bond with the opposing edge of the web in the sealing joint 8 which extends vertically over the packaging container. In such instance, the bridges 12 are placed in slight spaced-apart relationship to one another and may preferably be located at those parts of the sealing joint 8 which are disposed on the top and bottom 3 and 4, respectively, of the packaging container. Since the length of the bridges 12 is greater than the width of the sealing joint, the one, uninsulated end of the bridge will be located on and be accessible at the outside of the packaging material, while the opposing, uninsulated end of the bridge will be located inside the packaging container and be in direct contact with its contents. This is illustrated more closely in FIG. 5 where it will be apparent how a bridge 12 extends through the sealing joint 8. The location of the bridge 12 and the length of the insulating layer are adapted such that the one edge of the covering strip 19 may be sealed to the insulating layer 23 without covering the exposed, conducting layer 21 of the bridge 12. At the same time, the conducting layer is left exposed at the outside of the packaging container in that the insulating layer 23 terminates at its other end substantially at the incision surface in the end edge of the packaging laminate 9 located exteriorly in the sealing joint 8. In the finished embodiment of the packaging container shown in FIG. 1, both of the conductors will thus be electrically accessible from the outside and may in such instance serve as poles in electric quality control of the contents of the package.

On control of the contents, use is made of quality control equipment 24 which includes an impedance meter 25 which, via two conductors 26, is connected to each respective pole or bridge and thus to the contents at the opposite ends of the packaging container. The arrangement illustrated in FIG. 2 is also employed for quality control of the packed contents. In such instance however, use is made of but a single bridge 12, since the opposite pole consists of a surface contact plate 27 of electrically conductive material, against which the packaging container abuts with its one side wall 2. While, in the arrangement according to FIG. 1, it is the electrical properties of the product (the impedance) that are thus measured between the two bridges 12, in the embodiment according to FIG. 2 it is instead the electrical properties between the bridge and the surface contact plate 27 serving as opposite pole that are measured. Using this latter method, there is thus no possibility of realising a purely resistive measurement, since the plate and the conductive foil layer in the package will act as a capacitor placed in series with the impedance of the product. The method according to FIG. 2 will, however, give a much higher degree of sensitivity than could have been obtained wholly without direct contact with the contents, and this method is better suited for automatic control than the method employing two bridges.

When the described arrangements are reduced into practice, an electric quality control measurement is effected, after suitable incubation time and storage of the package at elevated temperature, in that a number of packages are caused to pass the electric measurement equipment 24. By repeated measurements, a range can be established within which the electric resistance is "normally" located when the pertinent combination of product type and package type is perfect and flawless. On the basis of these statistics, it is then possible to find and separate the individual packages in which micro biological activity has changed the electrical properties of the product in such a manner that they deviate from the established norm value in accordance with the foregoing. Only those packages need to be sorted out, while the remaining tested packages can be supplied to the customer without deviating in terms of quality from the remaining, flawless packages.

When it is desired to supplement the control and verification of the quality of the packed product with a control and verification of the integrity of the packaging container proper, i.e. control of the liquid- and bacteria-tightness of the packaging laminate 9, this may be put into effect at the same time or in a separate control operation. On control of the tightness of the packaging laminate 9, use is made as one pole of a bridge 12 of the described type, while the conductive barrier layer of the packaging laminate, e.g. of aluminium 16, is used as the opposite pole. More precisely, the one conductor of the measurement equipment is connected to a bridge 12 while the other conductor of the measurement equipment is connected to the aluminium layer 16 which is accessible from the outside along the incision edge of the packaging laminate 9, either along the longitudinal sealing joint 8 or along any of the two transverse sealing joints 6 and 7. In practice, such a connection implies that the packed contents 20 will, via the bridge 12, be connected to the electric measurement equipment, while the aluminium layer 16 extending over the entire surface of the packaging container will serve as the opposite pole. By measuring the conductivity between the poles, i.e. between the product and the aluminium foil, it becomes possible immediately to discover whether the layer 17 of thermoplastic located between the aluminium foil layer 16 and the contents 20 displays any ruptures or pores through which the contents 20 (and the current) may migrate and reach the aluminium foil 16. The measurement equipment employed may be of an extremely rudimentary nature and comprise a current source and a metre for the resistance in the circuit. As in the previously described control of the quality of the contents, it is possible using this equipment to establish, after a number of test measurements, a "normal" reaction, which form the basis of continued testing and rejection sorting of packages suffering from a damaged or leaking inner thermoplastic layer 17.

As has been mentioned above, the bridge or bridges extend in liquid- or bacteria-tight bond through the wall of the packaging container. When the bridges are placed in the sealing joints in the wall of the packaging container (and, for example, extend through sealing fins located at opposite ends of the packaging container), this is most simply realised in that the outer thermoplastic layers of the packaging material and bridges, respectively, are fused together by known technique. Naturally, in packaging containers of other types, the positioning of the bridges may be varied, and, for example, filamnent or needle-shaped bridges may technically extend in a sealed and tight manner through any part whatever of the packaging container.

Practical trials have shown that the described methods function well and that packaging material and packaging containers can be provided with bridges 12 without any major difficulty. Their positioning is not critical and it is not necessary, as shown, for example, in FIG. 1, to place the bridges on opposite sides of the packaging container. Poles placed at relatively short distances from one another may also make possible measurement with a sufficiently high degree of accuracy. Thus, the arrangement has proved to function well and, for the first time, to make for rational and dependable quality control and verification of the quality of both aseptically packed contents and aseptic packaging containers proper.

The present invention should not be considered as restricted to that described above and shown on the Drawings, many modifications being conceivable without departing from the spirit and scope of the appended Claims.

What is claimed is:

1. A method of quality control of packaging containers or the contents of packaging containers after filling and sealing of a packaging container of the type that is produced by forming of a flexible packaging material, comprising the steps of:

providing a packaging container having an inside, a sealing joint where the flexible material is overlapped and bonded to form a liquid-tight seal, and at least one electrically conductive bridge which extends through said sealing joint and serves as one pole; and measuring electrical properties of the packaging material wall or the contents of the packaging container through the at least one bridge.

2. The method as claimed in claim 1, wherein the providing step comprises providing a packaging container having two electrically conductive bridges forming two poles extending through the wall of the packaging container; and wherein said measuring step comprises measuring electrical properties of the contents of the packaging container between the two bridges.

3. The method as claimed in claim 1, wherein said providing step further comprises providing a packaging container having a second pole formed by a surface contact plate comprising electrically conductive material and located closely adjacent the outside of the packaging container; and wherein said measuring step comprises measuring electrical properties between the poles.

4. The method as claimed in claim 1, wherein said providing step comprises providing a packaging container of a flexible packaging material having a layer of electrically conductive material included in the flexible packaging material; and wherein said measuring step comprises measuring electrical properties between the one pole and the layer of electrically conductive material.

5. The method as claimed in claim 4, wherein said providing step comprises providing an exposed cut surface of said electrical conductive material layer; and wherein said measuring step comprises electrically connecting said exposed cut surface to a conductor.

6. The method as claimed in claim 1, further comprising the step of connecting the at least one pole to quality control equipment; and measuring electrical impedance at said at least one pole with said quality control equipment.

7. The method as claimed in claim 1, wherein said providing step comprises providing said at least one bridge having a length greater than the length of the sealing joint overlap in the flexible packaging material.

8. The method as claimed in claim 1, wherein said providing step further comprises providing a packaging container having a cover strip having two edges, and providing said at least one bridge including an insulating layer and a conducting layer, the cover strip positioned on the inside of the packaging container covering the sealing joint, one of said two edges of the cover strip sealing to said insulating layer and exposing a portion of said bridge conducting layer to the inside of the packaging container.

9. The method as claimed in claim 1, wherein said providing step further comprises providing said at least one bridge including an electrical conductor, a first insulating layer completely covering one side of said bridge electrical conductor, and a second insulating layer only partly covering a side of said bridge electrical conductor opposite said first insulating layer.

10. The method as claimed in claim 1, wherein said providing step further comprises providing said at least one bridge including an insulating layer extending through the sealing joint and terminating substantially at an exterior edge of the flexible packaging material at the sealing joint.

* * * * *